United States Patent [19]

Brittelli

[11] Patent Number: 4,877,892

[45] Date of Patent: Oct. 31, 1989

[54] CHIRAL GLYCIDYL AZIDES AS SYNTHETIC INTERMEDIATES TO OPTICALLY ACTIVE COMPOUNDS

[75] Inventor: David R. Brittelli, Nottingham, Pa.

[73] Assignee: E. I. Du Pont De Nemours and Company, Wilmington, Del.

[21] Appl. No.: 128,287

[22] Filed: Dec. 3, 1987

[51] Int. Cl.$^4$ .......................................... C07D 303/36
[52] U.S. Cl. .................................................... 549/552
[58] Field of Search ........................................ 549/552

[56] References Cited

U.S. PATENT DOCUMENTS

| | | | |
|---|---|---|---|
| 4,303,414 | 12/1981 | Frankel et al. | 44/63 |
| 4,408,063 | 10/1983 | Baldwin et al. | 549/518 |
| 4,588,824 | 5/1986 | Baldwin et al. | 549/453 |
| 4,601,344 | 7/1986 | Reed, Jr. et al. | 169/47 |
| 4,705,799 | 11/1987 | Gregory | 514/376 |

OTHER PUBLICATIONS

Chemical Abstract 107:201505v (1987).
Ingham, et al., *J. Org. Chem.*, 21, 373 (1956).
Sharpless, et al., *J. Org. Chem.*, 52, 667 (1987).

*Primary Examiner*—Asok Pal

[57] ABSTRACT

Chiral glycidyl azides, such as (2S)-glycidyl azide, are prepared, and they are useful as intermediates to prepare optically active compounds, particularly optically active, anti-bacterial oxazolidinones.

1 Claim, No Drawings

CHIRAL GLYCIDYL AZIDES AS SYNTHETIC INTERMEDIATES TO OPTICALLY ACTIVE COMPOUNDS

TECHNICAL FIELD

This invention relates to chiral glycidyl azides and processes for their preparation. The azides are useful as intermediates to prepare optically active compounds.

BACKGROUND OF THE INVENTION

Optical isomers of biologically interesting compounds should be regarded as two different entities because oftentimes they are transported differently, bound differently to receptors, metabolized differently and have different toxicities. Therefore, it is important to prepare optically active compounds before extensive biological and toxicological studies are initiated with a racemic mixture.

Racemic glycidyl azide has been prepared from epichlorohydrin by treatment with sodium azide and then aqueous sodium hydroxide [J. D. Ingham, W. L. Petty, and P. L. Nichols, Jr., *J. Org. Chem.*, 21, 373 (1956)].

Sharpless et al., *J. Org. Chem.*, 52, 667 (1987) describes that in the presence of acid catalyst, azide ion opens the epoxide ring of glycidyl p-nitrobenzoate at the C-3 position.

U.S. Pat. No. 4,303,414 issued to Frankel et al. on Dec. 1, 1981, discloses a composition containing glycidyl azides.

U.S. Pat. No. 4,408,063 issued to Baldwin on Oct. 4, 1983, discloses a process for preparing an enantiomer of epichlorohydrin which comprises treating an enantiomer of an alcohol of the formula:

$$Z-SO_2-O-CH_2-\overset{OH}{\underset{|}{CH}}-CH_2-X$$

wherein Z is phenyl, monosubstituted phenyl, $CF_3$ or $C_1$-$C_6$ alkyl and X is Cl or Br, with alkali metal glycolate and removing said epihalohydrin by distillation.

U.S. Pat. No. 4,588,824 issued to Baldwin on May 13, 1986, also discloses processes for preparing (S) or (R) epihalohydrin.

U.S. Pat. No. 4,601,344 issued to Reed et al. on July 22, 1986, discloses a composition containing glycidyl azide polymer.

None of the above mentioned references suggest the chiral glycidyl azides and processes for their preparation.

In U.S. Pat. No. 4,705,799 issued to Gregory on Nov. 10, 1987, optically active oxazolidinone azides and derivatives thereof are described.

SUMMARY OF THE INVENTION

According to the present invention, there is provided chiral glycidyl azides of the formula:

(I)    (II)

Also provided is a process for preparing compounds of formula (I) and (II), such a process being described in detail hereinafter.

DETAILED DESCRIPTION

Chiral, (2S)- or (2R)-glycidyl azides are prepared by the reaction of azide ion with the corresponding chiral glycidyl 4-nitrobenzenesulfonate as follows:

Scheme 1:

(I) or (II)

The source of azide ion can be one of those ionic alkali metal, quaternary ammonium or phosphonium azide salts, or others which are useful as sources of azide ion in non-aqueous solvents. The sodium salt is preferred because of its low cost and ready availability. The salt is preferably used in the presence of catalytic amounts of a solubilizing agent, such as a crown ether (e.g., 18-crown-6, 18-crown-5, etc.), a cryptand, and other cation-binding agents (well-known to those skilled in the art) which increase the reactivity of anions by ion-separation effects. Such agents are not absolutely necessary for the success of the reaction. The reaction is preferably carried out in a polar aprotic solvent, such as dimethylsulfoxide, N,N-dimethylformamide, N-methylpyrrolidone, 1,1,3,3-tetramethylurea, hexamethylphosphoramide, and others well-known to those skilled in the art. The reaction is preferably conducted at ice bath temperature, 0°–10° C., but may be carried out at temperatures of −78° to +80° C. The reaction is preferably conducted in a dry atmosphere to prevent contamination of the cool, hygroscopic polar aprotic solvents by atmospheric moisture.

The product glycidyl azides are easily isolated by pouring the reaction into water and extraction with a low boiling (<50° C.) water-immiscible organic solvent, such as ether or methylene chloride, followed by drying of the solvent and its careful removal under reduced pressure. The product glycidyl azides can be purified by distillation under reduced pressure, preferably at about 15 mm Hg or less at a temperature of about 45° C. or less. High temperature and pressure distillation should be avoided because glycidyl azide decomposes explosively at 190° C.

The optical purity of the product is assayed by conversion into a derivative whose absolute optical rotation is known. For example, the glycidyl azide is allowed to react with phenyl isocyanate as shown in Scheme 2 to yield an oxazolidinone, whose optical rotation is known from optically pure material which has been obtained by resolution (U.S. Pat. No. 4,705,799).

Scheme 2:

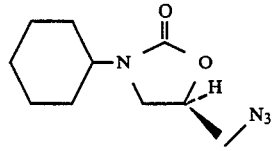

The chiral glycidyl 4-nitrobenzenesulfonate can be obtained by conventional esterification of optically active glycidol with 4-nitrobenzenesulfonyl chloride under a variety of conditions well-known to those skilled in the art of organic chemistry. Optically active glycidol is commercially available. Other sources of the optically active glycidols include enzymatic hydrolysis of racemic glycidyl esters to optically active glycidol and optically active glycidol of the other configuration (which may be chemically hydrolyzed to the corresponding glycidol of complementary absolute configuration) (W. E. Ladner and G. M. Whitesides, *J. Am. Chem. Soc.*, 106, 7520 (1984)), asymmetric epoxidation of allyl alcohol using optically-active catalysts (R. W. Hanson and K. B. Sharpless, *J. Org. Chem.*, 51, 1952 (1986)) and other less direct methods known to those in the art.

The invention can be further understood by the following example in which parts and percentages are by weight and temperatures in degrees Centigrade unless otherwise indicated.

EXAMPLE 1

Preparation of (2S)-Glycidyl azide (I)

PART A: Preparation of (2R)-Glycidyl-4-nitrobenzenesulfonate

To a solution of (2S)-glycidol (19.93 g, 0.27 mol) in methylene chloride (250 mL) at 0° under nitrogen was added triethylamine (37.5 mL, 0.27 mol) slowly. Then a solution of recrystallized p-nitrobenzenesulfonyl chloride (59.62 g, 0.27 mol) in methylene chloride (125 mL) was added at such a rate that the temperature did not rise above 15°. The mixture was stirred at ice-bath temperature for one hour. The precipitated triethylamine hydrochloride was filtered and the organic layer was washed with dilute acid, water, and dried (MgSO$_4$). Removal of the solvent in vacuo gave 63.3 g of the crude product which was recrystallized from n-butyl chloride to afford 56.2 g (80%) of (2R)-glycidyl 4-nitrobenzenesulfonate, m.p. 84°–86°; $[\alpha]_D = -24.6°$ (C=1.99, MeOH); Anal: calcd for C$_9$H$_9$NO$_6$S: C, 41.70; H, 3.50; N, 5.40; S, 12.37; Found: C, 41.84; H, 3.40; N, 5.04; S, 12.25.

PART B: Preparation of (2S)-Glycidyl azide (I)

To a solution of (2R)-glycidyl 4-nitrobenzenesulfonate (56.22 g, 0.217 mole) and 18-crown-6 (0.96 g, 3.6 mmol) in dry dimethylsulfoxide (110 mL) under nitrogen at 20° was added sodium azide (12.75 g, 0.196 mol) portionwise so that the temperature did not exceed 25°. The mixture was stirred for 3.5 hours and then diluted with water and extracted with ether. The ether was removed in vacuo at 15° after drying (MgSO$_4$) to yield 22.9 g of the crude product which was distilled to give 11.75 g (55%) of (2S)-glycidyl azide. b.p. 43° (20 mm Hg); $n_D^{24} = 1.4527$ (lit. $n_D^{20} = 1.4545$).

Assay of the Optical Purity of (2S)-Glycidyl Azide

To a solution of 1:1 lithium bromide/tri-n-butylphosphine oxide (0.7 mL, 0.35M in xylene) in xylene (10 mL) under nitrogen at 130° was added a solution of phenylisocyanate (0.67 mL) and (2S)-glycidyl azide (0.6 g) in xylene (5 mL). The mixture was refluxed for one hour and then allowed to cool to room temperature. The solvent was removed in vacuo and the residue, upon addition of n-butyl chloride, crystallized immediately. The collected solid was recrystallized from n-butyl chloride/petroleum ether (1:3) to give 0.8 g of (l)-5-azidomethyl-3-phenyl-2-oxazolidinone. m.p. 76°–77.5°; $[\alpha]_D^{19} = -156.6°$ (c=0.97, C$_2$H$_5$OH). For comparison, authentic optically active material had $[\alpha]_D^{25} = -160.0°$ (c=0.93, C$_2$H$_5$OH).

What is claimed is:

1. A chiral glycidyl azide of the formula:

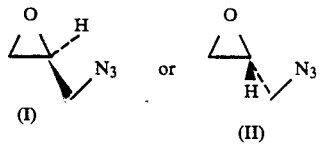

each said chiral azide of formula (I) or (II) being substantially free of the other chiral azide.

* * * * *